United States Patent [19]

George et al.

[11] Patent Number: 5,466,706
[45] Date of Patent: Nov. 14, 1995

[54] 9H-IMIDAZO[1,2-A]BENZIMIDAZOLE-3-ACETAMIDE DERIVATIVES, THEIR PREPARATION AND THEIR THERAPEUTIC APPLICATION

[75] Inventors: Pascal George, St Arnoult en Yvelines; Danielle De Peretti, Antony; Jocelyne Roy, Ris-Orangis; Jean-Paul Schmitt, Arpajon; Mireille Sevrin, Paris, all of France

[73] Assignee: Synthelabo, Le Plessis Robinson, France

[21] Appl. No.: 180,998

[22] Filed: Jan. 14, 1994

[30] Foreign Application Priority Data

Jan. 15, 1993 [FR] France ................................. 93 00337
Jul. 22, 1993 [FR] France ................................. 93 09013

[51] Int. Cl.$^6$ ............................. A61K 31; A61K 415; C07D 487/04
[52] U.S. Cl. ........................................ 514/394; 548/302.1
[58] Field of Search ........................ 548/302.1; 514/394

[56] References Cited

U.S. PATENT DOCUMENTS

| | | | |
|---|---|---|---|
| 3,732,243 | 5/1973 | Ogura et al. | 260/309.2 |
| 4,075,342 | 2/1978 | Sale et al. | 424/258 |
| 4,675,323 | 6/1987 | George et al. | 514/292 |
| 5,240,944 | 8/1993 | Tomiyama et al. | 514/322 |

FOREIGN PATENT DOCUMENTS 0172097  2/1986  European Pat. Off. .

OTHER PUBLICATIONS

Chemical Abstracts, 88(19), 135933u 1978 no month available.
Chemical Abstracts, 89(5), 43247r 1978 no month available.
Chemical Abstracts, 98(13), 107288a 1983 no month available.
Chemical Abstracts, 99(3), 22377z 1983 no month available.
Chemical Abstracts, 106(19), 156344h 1987 no month available.
Chemical Abstracts, 109(3), 22898v 1988 no month available.

Primary Examiner—Johann Richter
Assistant Examiner—Laura L. Stockton
Attorney, Agent, or Firm—Jacobson, Price, Holman & Stern

[57] ABSTRACT

Compound corresponding to the formula:

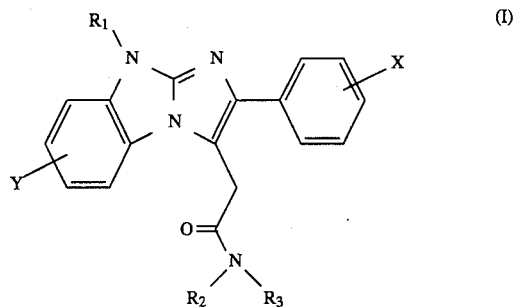

in which X represents one or more of hydrogen, halogen, alkyl, trifluoromethyl, alkoxy, alkylthio, methylsulphonyl, cyano, ethoxycarbonyl, aminocarbonyl and carboxy, Y represents one or more of hydrogen, halogens, alkyl, trifluoromethyl, methoxy and trifluoromethoxy, $R_1$ represents hydrogen, alkyl, phenylmethyl, 2-phenylethyl, acetyl or alkoxycarbonyl, $R_2$ and $R_3$ each represent hydrogen, alkyl which is optionally substituted, prop-2-enyl, prop-2-ynyl, phenyl, 1-(phenylmethyl)piperidin-4-yl, or 1-[(cyclohexen-1-yl)methyl]piperidin-4-yl, or alternatively $R_2$ and $R_3$ form, with the nitrogen atom carrying them, an optionally substituted heterocycle. These compounds are useful as hypnotic, anxiolytic and anticonvulsant agents.

7 Claims, No Drawings

9H-IMIDAZO[1,2-A]BENZIMIDAZOLE-3-ACETAMIDE DERIVATIVES, THEIR PREPARATION AND THEIR THERAPEUTIC APPLICATION

The present invention relates to 9H-imidazo[1,2-a]benzimidazole-3-acetamide derivatives, their preparation and their therapeutic use.

The compounds of the invention correspond to the formula:

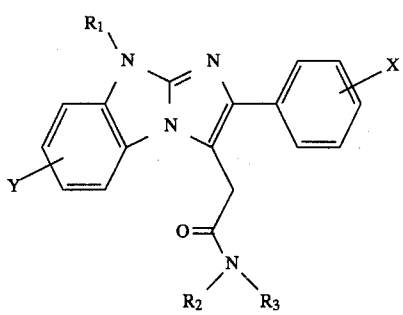

in which

X represents one or more atoms or groups chosen from hydrogen, fluorine, chlorine, bromine, $(C_1-C_3)$alkyl, trifluoromethyl, $(C_1-C_3)$alkoxy, $(C_1-C_3)$alkylthio, methylsulphonyl, cyano, ethoxycarbonyl, aminocarbonyl, and carboxy, Y represents one or more atoms or groups chosen from hydrogen, fluorine, chlorine, bromine and $(C_1-C_4)$alkyl, trifluoromethyl, methoxy and trifluoromethoxy, $R_1$ represents a hydrogen atom, $(C_1-C_3)$alkyl, phenylmethyl, 2-phenylethyl, acetyl or $(C_1-C_3)$alkoxycarbonyl, are the same or different and $R_2$ and $R_3$ each represents, a hydrogen atom; $(C_1-C_5)$alkyl which is linear, branched or cyclic, and optionally substituted by one or more fluorine atoms, or by methoxy, phenoxy, dimethylamino, phenyl or imidazol-4-yl; prop-2-enyl group, prop-2-ynyl; phenyl; 1-(phenylmethyl)piperidin-4-yl; or 1-[(cyclohexen-1-yl)methyl]piperidin-4-yl, or alternatively $R_2$ and $R_3$ form together with the nitrogen atom carrying them, a pyrrolidin-1-yl, 3-ethoxypyrrolidin-1-yl, piperidin-1-yl, 4-(phenylmethyl)piperidin-1-yl, spiro(dioxolane-2,4'-piperidin)-1'-yl, 3-(phenoxymethyl) piperidin-1-yl, 4-(phenoxymethyl) piperidin-1-yl, hexahydroazepin-1-yl, 4-methylpiperazin-1-yl, 4-(phenylmethyl)piperazin-1-yl, morpholin-1-yl or thiomorpholin-1-yl group.

The compounds of the invention can be provided as free bases or as acid addition salts.

Preferred compounds of the invention include those in which X is in position 4 and represents a hydrogen, fluorine or methyl, those in which Y is in position 6 and represents a hydrogen, fluorine or methyl, those in which $R_1$ represents hydrogen or methyl, and those in which $R_2$ and $R_3$ each represent, independently of one another, hydrogen or methyl.

In accordance with a feature of the invention, the compounds of formula I are prepared by a process illustrated in Scheme 1 which follows.

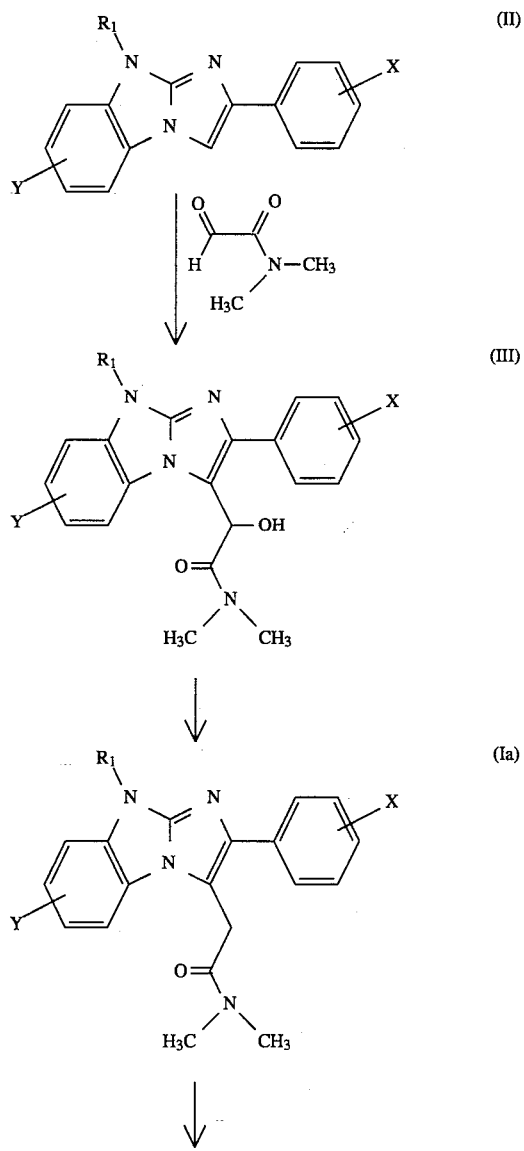

-continued
Scheme 1

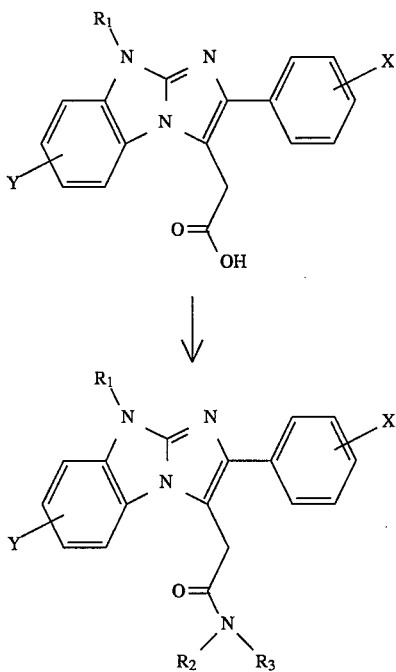

A 9H-imidazo[1,2-a]benzimidazole derivative of formula (II) (in which X, Y and $R_1$ are as defined above) is reacted with N,N-dimethylglyoxamide (prepared in situ from 2,2-diethoxy-N,N-dimethylacetamide, as described in Patent Application EP-251859) in a protic solvent such as acetic acid at a temperature of 20° to 80° C. The α-hydroxyacetamide derivative of formula (III) is then treated with a polyhalide of sulphuric or phosphoric acid, for example thionyl chloride or phosphorus oxychloride, or any other equivalent agent, in an inert solvent, for example a chlorine-containing or ethereal solvent such as dichloromethane or tetrahydrofuran, at a temperature of 20° to 80° C., to form the corresponding α-haloacetamide derivative. The latter is then reacted either with a reducing agent such as a simple or complex alkali metal hydride, for example sodium or potassium borohydride, in a protic solvent, for example an aliphatic alcohol such as methanol or ethanol, or in a water-miscible inert solvent, for example dioxane or tetrahydrofuran, at a temperature of −40° to 40° C., either with a reducing agent such as an alkali metal hyposulphite or dithionite, for example sodium hyposulphite or dithionite, or alternatively with sodium hydroxymethylsulphoxylate (Rongalite®), in an inert solvent, for example a chlorine-containing solvent such as dichloromethane, optionally in the presence of a water-miscible inert cosolvent, for example N,N-dimethylformamide or N-methylpyrrolidone, at a temperature of 20° to 40° C.

An N,N-dimethylacetamide derivative of formula (Ia) is thus obtained with corresponds to the formula (I) when $R_2$ and $R_3$ each represent a methyl group.

If it is desired to prepare a compound of formula (I) in which $R_2$ and $R_3$ each do not represent a methyl group, the compound of formula (Ia) is converted into an acid of formula (IV), by hydrolysis by means of a strong base, for example sodium hydroxide or potassium hydroxide, in a protic solvent, for example ethanol or 2-methoxyethanol, in the presence of water.

The acid of formula (IV) is then reacted with N,N'-carbonyldiimidazole, in an inert solvent, for example a chlorine-containing or ethereal solvent such as dichloromethane or tetrahydrofuran, at a temperature of 20° to 50° C., to obtain the corresponding imidazolide, and finally the latter is treated with an amine of formula $HNR_2R_3$ (in which $R_2$ and $R_3$ are as defined above) at a temperature of 0° to 25° C.

The compounds of formulae (III) and (IV) are new and form part of the invention, as synthesis intermediates for the process illustrated by the preceding scheme.

The derivatives of formula (II) can be prepared according to any method described in the literature, for example in J. Het. Chem., 2, 287 (1965), Khim. Geterosikl. Soedin. 133 (1967), J. Med. Chem., 15, 923 (1972).

The compounds of the invention can also be prepared according to the process illustrated in Scheme 2 which follows.

Scheme 2

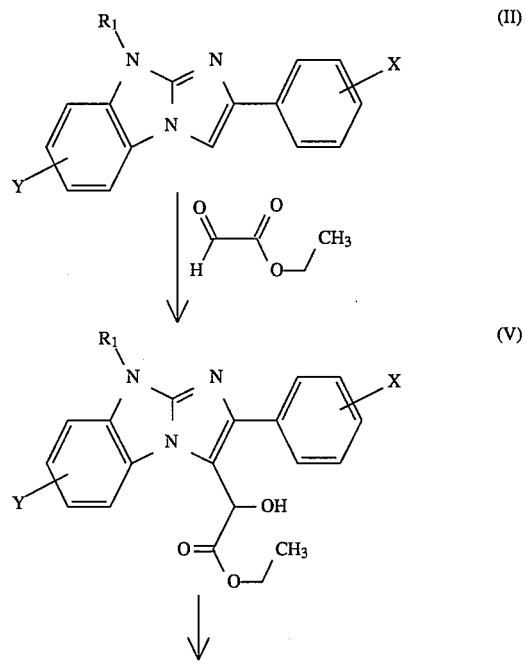

-continued
Scheme 2

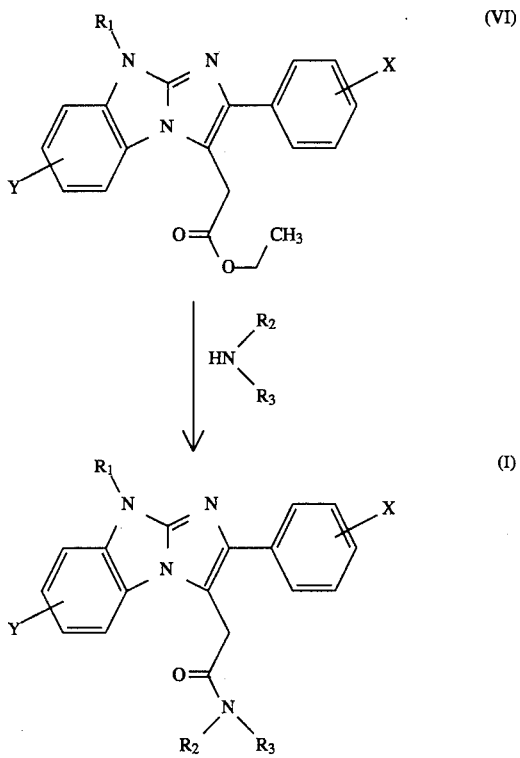

A 9H-imidazo[1,2-a]benzimidazole derivative of formula (II) (in which X, Y and $R_1$ are as defined above) is reacted with ethyl glyoxylate (which is prepared in Situ by means of ethyl 2,2-diethoxy acetate as described in Patent Application EP-251859) in a protic solvent such as acetic acid at a temperature of 20° to 80° C. The ethyl α-hydroxyacetate derivative of formula (V) is then treated with a polyhalide of sulphuric or phosphoric acid, for example thionyl chloride or phosphorus oxychloride, or any other equivalent agent, in an inert solvent, for example a chlorine-containing or ethereal solvent such as dichloromethane or tetrahydrofuran, at a temperature of 20° to 80° C., to form the corresponding ethyl α-haloacetate derivative. The latter is then reacted either with a reducing agent such as a simple or complex alkali metal hydride, for example sodium or potassium borohydride, in a protic solvent, for example an aliphatic alcohol such as methanol or ethanol, or in a water-miscible inert solvent, for example dioxane or tetrahydrofuran, at a temperature of −40° to 40° C., or with a reducing agent such as an alkali metal hyposulphite or dithionite, for example sodium hyposulphite or dithionite, or alternatively with sodium hydroxymethylsulphoxylate (Rongalite®), in an inert solvent, for example a chlorine-containing solvent such as dichloromethane, optionally in the presence of a water-miscible inert cosolvent, for example N,N-dimethylformamide or N-methylpyrrolidone, at a temperature of 20° to 40° C.

A compound of formula (VI) is thus obtained which is then reacted with an excess of amine of formula $HNR_2R_3$ (in which $R_2$ and $R_3$ are as defined above) in a protic solvent such as an alcohol, for example methanol or ethanol, at a temperature of 0° to 70° C.

The compounds of formula (VI) are new and form part of the invention, as synthesis intermediates for the process illustrated by scheme 2.

The Examples which follow illustrate the preparation of some compounds of the invention. Elemental microanalyses, and the IR and NMR spectra confirm the structures of the compounds obtained. The numbers indicated in brackets in the titles of the examples correspond to those in the 1st column of Table 1 given later. This table illustrates the chemical structures and the physical properties of a few compounds of formula (I).

EXAMPLE 1 (COMPOUND NO.2)

N,N-dimethyl-2-phenyl-9H-imidazo[1,2-a]benzimidazole-3-acetamide.

1.1. α-Hydroxy-N,N-dimethyl-2-phenyl-9H-imidazo[1,2-a]-benzimidazole-3-acetamide.

13.5 g (0.077 mol) of 2,2-diethoxy-N,N-dimethylacetamide and 1.7 ml (0.019 mol) of 35% hydrochloric acid are mixed in 125 ml of acetic acid and the mixture is heated while stirring in a bath at 45° C. for 1 h. There are then added 6.3 g (0.077 mol) of sodium acetate and then, after 15 min, 6 g (0.026 mol) of 2-phenyl- 9H-imidazo[1,2-a]benzimidazole, and the heating and the stirring are maintained for 10 h. The mixture is evaporated under reduced pressure and at a temperature of less than 40° C. The residue is taken up in water and dichloromethane, ammonium hydroxide is added up to pH 11, and an insoluble matter is removed by filtration. The organic phase is separated, washed with water, and dried over sodium sulphate. The solvent is evaporated under reduced pressure, and the residue is crystallized from diethyl ether, drained, washed with diethyl ether, and dried under vacuum. 6 g of compound are obtained. Melting point: 215° C. (decomposition). 1.2 N,N-dimethyl-2-phenyl-9H-imidazo[1,2-a]benzimidazole-3-acetamide.

6 g (0.018 mol) of α-hydroxy-N,N-dimethyl-2-phenyl-9H-imidazo[1,2-a]benzimidazole-3-acetamide are treated with 30 ml of thionyl chloride in 300 ml of dichloromethane at room temperature for 24 h. The solvent and the excess thionyl chloride are evaporated under reduced pressure. The residue is crystallized from diethyl ether, drained and dried.

7.1 g of α-chloro-N,N-dimethyl-2-phenyl-9H-imidazo[1,2-a]benzimidazole-3-acetamide hydrochloride are obtained, which are reduced 8.3 g (0.054 mol) of Rongalite® in 300 ml of dichloromethane at room temperature for 24 h. The suspension is taken up in a saturated aqueous solution of sodium bicarbonate, and the organic phase is separated, dried over sodium sulphate, and evaporated under reduced pressure. The residue is crystallized from diethyl ether, drained, washed with diethyl ether, dried and recrystallized from ethanol. 2.35 g of compound are obtained. Melting point: 268°–271° C. (decomposition)

EXAMPLE 2 (COMPOUND NO.39)

N,9-dimethyl-2-(4-methylphenyl)-9H-imidazo[1,2-a]benzimidazole-3-acetamide.

2.1 α-Hydroxy-N,N,9-trimethyl-2-(4-methylphenyl)-9H-imidazo[ 1,2-a]benzimidazole-3-acetamide.

38.2 g (0.22 mol) of 2,2-diethoxy-N,N-dimethylacetamide and 4.85 ml (0.055 mol) of 35% hydrochloric acid are dissolved in 350 ml of acetic acid, and the mixture is heated while stirring in a bath at 45° C. for 1 h. There are then added 17.9 g (0.22 mol) of sodium acetate and, after 15 min, 19 g (0.073 mol) of 9-methyl-2-(4-methylphenyl)-9H-imidazo[1,2-a]benzimidazole, and the heating and stirring are maintained for 2 h 30 min. The mixture is evaporated under reduced pressure at a temperature of less than 40° C. The residue is taken up in 200 ml of dichloromethane and 200 ml of ice-cold water. Ammonium hydroxide is added up to pH 11. Insoluble matter is removed by filtration. The organic phase is separated, washed with water, and dried over sodium sulphate. The solvent is evaporated under reduced pressure, and the residue is crystallized from diethyl ether, drained, washed with diethyl ether and dried under vacuum. 21.8 g of compound are obtained. Melting point: 192°–193° C.

2.2 N,N,9-trimethyl-2-(4-methylphenyl)-9H-imidazo[1,2-a]benzimidazole-3-acetamide.

19.2 g (0.053 mol) of α-hydroxy-N,N,9-trimethyl-2-(4-methylphenyl)-9H-imidazo[1,2-a]benzimidazole-3-acetamide are dissolved in 960 ml of dichloromethane and the solution is treated with 96 ml of thionyl chloride at room temperature for 24 h. The solvent and the excess thionyl chloride are evaporated under reduced pressure. The residue is crystallized from diethyl ether. The solid obtained is drained, washed with diethyl ether and rapidly air-dried.

21.9 g of α-chloro-N,N,9-trimethyl-2-(4-methylphenyl)-9H-imidazo[1,2-a]benzimidazole-3-acetamide hydrochloride are obtained which are reduced with 31.1 g (0.154 mol) of Rongalite® in 960 ml of dichloromethane at room temperature for 36 h. The mixture is washed with a 4% aqueous solution of sodium bicarbonate, and then with water, and the organic phase is dried over sodium sulphate. The solvent is evaporated under reduced pressure. The residue is taken up in diethyl ether, and the solid is separated by filtration, washed with diethyl ether and dried under vacuum. 14.1 g of compound are obtained. Melting point: 195°–196° C.

2.3 9-Methyl-2-(4-methylphenyl)-9H-imidazo[1,2-a]benzimidazole-3-acetic acid.

11 g (31.7 mmol) of N,N,9-trimethyl-2-(4-methylphenyl)-9H-imidazo[1,2-a]benzimidazole-3-acetamide are dissolved in 330 ml of 2-methoxyethanol. A solution of 6.35 g (0.159 mol) of sodium hydroxide pellets in 44 ml of water is added, and the mixture is refluxed for 10 h. The solvent is evaporated under reduced pressure. The residue is taken up in water. A slight insoluble residue is removed by filtration, and the pH of the filtrate is adjusted to 5 with acetic acid. A precipitate is obtained which is separated by filtration, washed with water, and dried under vacuum. It is taken up in ethanol, filtered, washed with ethanol, and dried under vacuum. 6.7 g of compound are obtained. Melting point: 250°–254° C. (decomposition).

2.4 N,9-dimethyl-2-(4-methylphenyl)-9H-imidazo[1,2-a]benzimidazole-3-acetamide.

A suspension of 1.9 g (0.006 mol) of 9-methyl-2-(4-methylphenyl)-9H-imidazo[1,2-a]benzimidazole-3-acetic acid is prepared in 50 ml of dry tetrahydrofuran, 1.45 g (0.009 mol) of N,N'-carbonyldiimidazole are added, in small portions, under an inert atmosphere and the mixture is stirred at room temperature for 2 h. The mixture is cooled in an ice-cold water bath, and treated with an excess of dry methylamine. Stirring is maintained for 16 h at room temperature. The solvent is evaporated under reduced pressure, and the residue is taken up in water, separated by filtration, washed with water, dried under vacuum and purified by recrystallization from methanol. 1 g of compound is obtained. Melting point: 251°–252° C.

EXAMPLE 3 (COMPOUND NO.57)

9-Ethyl-2-(4-methylphenyl)-9H-imidazo[1,2-a]benzimidazole-3-acetamide. 3.1

9-Ethyl-α-hydroxy-N,N-dimethyl-2-(4-methylphenyl)-9H-imidazo[1,2-a]benzimidazole-3-acetamide.

27 g (0.145 mol) of 2,2-diethoxy-N,N-dimethylacetamide and 4 ml (0.038 mol) of 35% hydrochloric acid are dissolved in 150 ml of acetic acid, and the mixture is heated while stirring it in a bath at 40° C. for 1 h. 12.7 g (0.145 mol) of sodium acetate are added and then, after 15 min, 14 g (0.05 mol) of 9-ethyl-2-(4-methylphenyl)-9H-imidazo[1,2-a]benzimidazole in solution in 100 ml of acetic acid. The heating and stirring are maintained for 3 h. The solvent is evaporated under reduced pressure and at a temperature of less than 40° C. The residue is taken up in water and dichloromethane, the pH is adjusted to 11 with ammonium hydroxide, and insoluble matter is removed by filtration. The organic phase is separated, washed with water, and dried over sodium sulphate. The solvent is evaporated under reduced pressure, and the residue is crystallized from diethyl ether, drained, washed and dried under vacuum. 14.2 g of compound are obtained, which is used as it is in the next stage.

3.2 9-Ethyl-N,N-dimethyl-2-(4-methylphenyl)-9H-imidazo[1,2-a]benzimidazole-3-acetamide.

14 g (0.037 mol) of 9-ethyl-α-hydroxy-N,N-dimethyl-2-(4-methylphenyl)-9H-imidazo[1,2-a]benzimidazole-3-acetamide are treated with 50 ml of thionyl chloride in 500 ml of dichloromethane at room temperature for 24 h. The solvent and excess thionyl chloride are evaporated under reduced pressure. The residue is crystallized from diethyl ether, and rapidly dried. It is then dissolved in 500 ml of dichloromethane. 24 g (0.156 mol) of Rongalite® are added and the mixture is stirred at room temperature for 24 h. The insoluble matter is removed by filtration. The filtrate is washed with aqueous sodium bicarbonate solution and then with water, and dried over sodium sulphate. The solvent is evaporated under reduced pressure and the residue is purified by silica gel column chromatography, eluting with a 97.5/2.5 mixture of dichloromethane/methanol. 4.5 g of compound are obtained in base form. Melting point: 90° C.

The hydrochloride is prepared using a 0.1N hydrochloric acid solution in propan-2-ol. Melting point: 247°–251° C. (decomposition).

3.3 9-Ethyl-2-(4-methylphenyl)-9H-imidazo[1,2-a]benzimidazole-3-acetic acid.

3.45 g (0.0096 mol) of 9-ethyl-N,N-dimethyl-2-(4-methylphenyl)-9H-imidazo[1,2-a]benzimidazole-3-acetamide are dissolved in 100 ml of 2-methoxyethanol. A solution of 2.2 g (0.055 mol) of sodium hydroxide in 15 ml of water is added and the mixture is refluxed for 13 h. The solvent is evaporated under reduced pressure. The residue is taken up in water. Insoluble matter is removed by filtration. Acetic acid is added to pH 5. The precipitate is separated by filtration, drained, washed and dried. 2.38 g of compound are obtained, which is used as it is in the next stage. Melting point: 2°–218° C. (decomposition).

3.4 9-Ethyl-2-(4-methylphenyl)-9H-imidazo[1,2-a]benzimidazole-3-acetamide.

A suspension of 1.1 g of 9-ethyl-2-(4-methylphenyl)-9H-imidazo[1,2-a]benzimidazole-3-acetic acid is prepared in 30 ml of dry tetrahydrofuran, 0.9 g (0.0056 mol) of N,N'-carbonyldiimidazole is added in small portions and the mixture is stirred at room temperature for 2 h. The solution obtained is treated with an excess of dry ammonia, and stirring is maintained at room temperature for 8 h. The solvent is evaporated under reduced pressure and the residue is purified by recrystallization from a mixture of methanol and propan-2-ol. 0.77 g of compound is obtained. Melting point: 25°–254° C. (decomposition).

EXAMPLE 4 (COMPOUND NO.11).

N,N,6,9-Tetramethyl-2-phenyl-9H-imidazo[1,2-a]benzimidazole-3-acetamide.

4.1 α-Hydroxy-N,N,6,9-tetramethyl-2-phenyl-9H-imidazo[1,2-a]benzimidazole-3-acetamide.

28.03 g (0.16 mol) of 2,2-diethoxy-N,N-dimethylacetamide and 3.6 ml (0.0432 mol) of concentrated hydrochloric acid are dissolved in 130 ml of acetic acid and the mixture is heated for 1 h at 40° C. 13.1 g (0.16 mol) of sodium acetate are then added, and the mixture is stirred for 15 min. Then a solution of 13.81 g (0.0528 mol) of 6,9-dimethyl-2-phenyl-9H-imidazo[1,2-a]benzimidazole in 70 ml of acetic acid is added and the heating is maintained at 40°–45° C. for 3 h. The solvent is evaporated under reduced pressure and at a temperature of less than 40° C. The residue is taken up in 200 ml of dichloromethane and 200 ml of ice-cold water and the pH is adjusted to 10–11 with sodium hydroxide. The insoluble matter is removed by filtration. The organic phase is separated by decantation, washed with water, and dried over sodium sulphate and the solvent is evaporated under reduced pressure. The residue is dried under reduced pressure in the presence of phosphorus pentoxide. 12.73 g of solid are obtained, which is used as it is in the next stage.

4.2. N,N,6,9-Tetramethyl-2-phenyl-9H-imidazo[1,2-a]benzimidazole-3-acetamide.

12.73 g (0.035 mol) of α-Hydroxy-N,N,6,9-tetramethyl-2-phenyl-9H-imidazo[1,2-a]benzimidazole-3-acetamide are treated with 75 ml of thionyl chloride in 250 ml of dichloromethane for 24 h. The solvent is evaporated and the excess thionyl chloride is evaporated under reduced pressure. The residue is taken up in toluene and the mixture is again evaporated. The residue is taken up in 600 ml of dichloromethane, 22 g of Rongalite® are added and the mixture is stirred for 48 h. Insoluble matter is removed by filtration. The filtrate is washed with water, with an aqueous sodium bicarbonate solution and again with water. The organic phase is dried over sodium sulphate, and the solvent is evaporated under reduced pressure. 10.36 g of solid are isolated which are purified by silica gel column chromatography, eluting with a chloroform/methanol 90/10 mixture. 7.86 g of product are isolated of which 1.3 g are removed and dissolved in dichloromethane. The solution is filtered and the filtrate is evaporated under reduced pressure. The residue is treated with carbon black in methanol, the suspension is filtered, the methanol is evaporated under reduced pressure, and the residue is dried under vacuum. 0.9 g of white solid are obtained. Melting point: 222°–223° C.

EXAMPLE 5 (COMPOUND NO.10)

N,6,9-Trimethyl-2-phenyl-9H-imidazo[1,2-a]benzimidazole-3-acetamide.

5.1. 6,9-Dimethyl-2-phenyl-9H-imidazo[1,2-a]benzimidazole- 3-acetic acid.

5.2 g (0.015 mol) of N,N,6,9-tetramethyl-2-phenyl-9H-imidazo[1,2-a]benzimidazole-3-acetamide are dissolved in 130 ml of 2-methoxyethanol, and a solution of 3.5 g (0.0875 mol) of sodium hydroxide in 20 ml of water is added. The mixture is refluxed for 3 h 30 min. The solvent is evaporated under reduced pressure. The residue is taken up in 150 ml of water and the pH is adjusted up to 5 with 10 ml of acetic acid. The insoluble matter is collected by filtration, and dissolved in 100 ml of 2-methoxyethanol in the presence of 4 g of potassium hydroxide and 20 ml of water. The mixture is again heated for 3 h 30 min. The solvent is evaporated under reduced pressure. The residue is taken up in water and acetic acid is added up to pH =5. The insoluble matter is collected by filtration, washed with water and dried. 4.51 g of solid are obtained, which is used as it is in the next stage.

5.2. N,6,9-trimethyl-2-phenyl-9H-imidazo[1,2-a] benzimidazole-3-acetamide.

A suspension of 1.5 g (0.0047 mol) of 6,9-dimethyl-2-phenyl-9H-imidazo[1,2-a]benzimidazole-3-acetic acid is prepared in 50 ml of dry tetrahydrofuran, 1.22 g (0.0075 mol) of N,N'-carbonyldiimidazole are added thereto and the mixture is stirred for 2 h. The solution obtained is treated with an excess of dry gaseous methylamine and stirred for several hours. The solvent is evaporated under reduced pressure. The residue is taken up in water and the solid residue is isolated by filtration. After drying, the product is purified by silica gel column chromatography, eluting with a dichloromethane/methanol 95/5 mixture. The product obtained is then treated with a hydrochloric acid solution. The precipitate is collected by filtration and treated with an excess of ammonium hydroxide up to a pH of 9 to 10. A solid is isolated which is washed with water and dried. 0.79 g of product is obtained. Melting point: 251°–253° C.

EXAMPLE 6 (COMPOUND NO.9)

6,9-Dimethyl-2-phenyl-9H-imidazo[1,2-a]benzimidazole-3-acetamide.

A suspension of 1.5 g (0.0047 mol) of 6,9-dimethyl-2-phenyl-9H-imidazo[1,2-a]benzimidazole-3-acetic acid is prepared in 50 ml of dry tetrahydrofuran. 1.22 g (0.0075 mol) of N,N'-carbonyldiimidazole are added thereto and the mixture is stirred for 2 h at 40°–45° C. The solution obtained is then treated with an excess of dry ammonia and stirred for 2 h. The solvent is evaporated under reduced pressure. The residue is washed with water and dried. The product obtained is purified by silica gel column chromatography, eluting with a chloroform/acetone 95/5 mixture and 0.71 g of product is isolated. Melting point: 247°–249° C. (decomposition).

EXAMPLE 7 (COMPOUND NO.17)

6-Chloro-N,N,9-trimethyl-2-phenyl-9H-imidazo[1,2-a] benzimidazole-3-acetamide.

7.1. 6-Chloro-α-hydroxy-N,N,9-trimethyl-2-phenyl-9H-imidazo[1,2-a]benzimidazole-3-acetamide.

26.3 g (0.148 mol) of 2,2-diethoxy-N,N-dimethylacetamide and 3.5 ml (0.042 mol) of concentrated hydrochloric acid are dissolved in 130 ml of acetic acid and the mixture is heated for 1 h at 40° C. 12.3 g (0.15 mol) of sodium acetate are then added. The mixture is stirred for 15 min and a solution of 14.19 g (0.05 mol) of 6-chloro-9-methyl-2-phenyl-9H-imidazo[1,2-a]benzimidazole in 70 ml of acetic acid is then added. The mixture is stirred for 3 h at 40° C., and the solvent is then evaporated under reduced pressure at a temperature of less than 40° C. The residue is taken up in 200 ml of ice-cold water and 200 ml of dichloromethane. The mixture is stirred for 5 min and then treated with an excess of ammonium hydroxide up to basic pH. Insoluble matter is removed by filtration, and the organic phase is decanted, washed with water and dried over sodium sulphate. The solvent is evaporated under reduced pressure and 16.5 g of solid are obtained, which is used as it is in the next stage.

7.2 6-Chloro-N,N,9-trimethyl-2-phenyl-9H-imidazo[1,2-a] benzimidazole-3-acetamide.

16.5 g (0.043 mol) of 6-chloro-α-hydroxy-N,N,9-trimethyl- 2-phenyl-9H-imidazo[1,2-a]benzimidazole-3-acetamide are treated with 90 ml of thionyl chloride in 250 ml of dichloromethane. The mixture is stirred for 6 h and allowed to stand overnight. The solvent and excess thionyl chloride are evaporated under reduced pressure. The residue is taken up in toluene and the mixture is again evaporated. The residue is dissolved in 800 ml of dichloromethane and treated with 26.5 g of Rongalite®. The mixture is stirred for 48 h and the insoluble matter is then separated by filtration. The organic phase is washed with sodium bicarbonate and then with water. The solvent is evaporated under reduced pressure and the residue is taken up in pentane. 14.96 g of solid are obtained which are purified by silica gel column chromatography, eluting with a dichloromethane/methanol 95/5 mixture. 8.59 g of product are isolated, of which a sample of 1.4 g is taken and dissolved in dichloromethane. The solution is filtered and the filtrate is concentrated under reduced pressure. The residue is treated with carbon black in methanol, and the product is then recrystallized from an N,N-dimethylformamide/water 2/1 mixture and 0.98 g of solid is obtained. Melting point: 233°–236° C.

EXAMPLE 8 (COMPOUND NO.16)

6-Chloro-N,9-dimethyl-2-phenyl-9H-imidazo[1,2-a]benzimidazole-3-acetamide.

8.1. 6-Chloro-9-methyl-2-phenyl-9H-imidazo[1,2-a]benzimidazole-3-acetic acid.

7 g (0.019 mol) of 6-chloro-N,N,9-trimethyl-2-phenyl-9H-imidazo[1,2-a]benzimidazole-3-acetamide are dissolved in 150 ml of 2-methoxyethanol, 4.5 g (0.112 mol) of sodium hydroxide in solution in 25 ml of water are added and the mixture is refluxed for 3 h. The solvent is evaporated under reduced pressure, and the residue is taken up in water and the solution obtained is acidified with acetic acid. The solid is collected by filtration, and dissolved in a mixture of 100 ml of 2-methoxyethanol, 20 ml of water and 5 g (0.089 mol) of potassium hydroxide. The mixture is stirred and refluxed for 8 h 30 min. The solvent is evaporated under reduced pressure. The residue is taken up in water and acidified to pH =5 with acetic acid. The insoluble matter is isolated by filtration and dried. 5.76 g of solid are obtained. Melting point: 245°–250° C. (decomposition).

8.2. 6-Chloro-N,9-dimethyl-2-phenyl-9H-imidazo[1,2-a]benzimidazole-3-acetamide.

A suspension of 1.5 g (0.044 mol) of 6-chloro-9-methyl-2-phenyl-9H-imidazo[1,2-a]benzimidazole-3-acetic acid is prepared in 50 ml of dry tetrahydrofuran, 1.15 g (0.071 mol) of N,N'-carbonyldiimidazole are added thereto and the mixture is stirred for 18 h. The solution is then treated with an excess of dry gaseous methylamine and again stirred for 6 h. The solvent is evaporated under reduced pressure. The residue is treated with water, sodium bicarbonate solution and again with water. The insoluble matter is collected by filtration and dried. It is purified by silica gel column chromatography, eluting with a dichloromethane/methanol 97/3 mixture. The product obtained is treated with a hydrochloric acid solution. The precipitate is collected by filtration and treated with excess of ammonium hydroxide. The product obtained is recrystallized from an N,N-dimethylformamide/water 75/25 mixture and then dried at 100° C. under vacuum. 0.8 g of solid is obtained. Melting point: 272°–273.5° C. (decomposition).

EXAMPLE 9 (COMPOUND NO.15)

6-Chloro-9-methyl-2-phenyl-9H-imidazo[1,2-a]benzimidazole-3-acetamide.

The procedure is carried out in the same manner as that described for Example 6, starting with 1.5 (0.044 mol) of 6-chloro-9-methyl-2-phenyl-9H-imidazo[1,2-a]benzimidazole-3-acetic acid. 0.9 g of the amide is obtained after purification. Melting point: 253°–254° C. (decomposition).

EXAMPLE 10 (COMPOUND No.20)

7-Chloro-N,N,9-trimethyl-2-phenyl-9H-imidazo[1,2-a]benzimidazole-3-acetamide. 10.1
7-Chloro-α-hydroxy-N,N,9-trimethyl-2-phenyl-9H-imidazo[1,2-a]benzimidazole-3-acetamide.

42.05 g (0.24 mol) of 2,2-diethoxy-N,N-dimethylacetamide and 5.6 ml (0.067 mol) of concentrated hydrochloric acid are dissolved in 150 ml of acetic acid, and the mixture is stirred at 40° C. for 1 h. 19.65 g (0.24 mol) of sodium acetate are then added thereto, and the mixture is stirred for 15 to 20 min. A suspension of 22.45 g (0.08 mol) of 7-chloro-6-methyl-2-phenyl-9H-imidazo[1,2-a]benzimidazole in 150 ml of acetic acid is then added. The mixture is stirred for 4 h at 40°–50° C. The solvent is evaporated under reduced pressure at a temperature of less than 45° C. The residue is taken up in 300 ml of ice-cold water and 250 ml of dichloromethane. The mixture is made alkaline with sodium hydroxide. The insoluble matter is separated by filtration, and washed with dichloromethane. The filtrate is separated, and the organic phase is dried over sodium sulphate. The solvent is evaporated under reduced pressure. 25 g of product are obtained, which is used as it is in the next stage.

10.2. 7-Chloro-N,N,9-trimethyl-2-phenyl-9H-imidazo[1,2-a]benzimidazole-3-acetamide.

21.05 g (0.0548 mol) of 7-chloro-α-hydroxy-N,N,9-trimethyl- 2-phenyl-9H-imidazo[1,2-a]benzimidazole-3-acetamide are treated with 115 ml of thionyl chloride and the mixture is stirred for 9 h. The excess thionyl chloride is evaporated under reduced pressure. The residue is taken up in toluene and the latter is evaporated. The residue is dissolved in 800 ml of dichloromethane, 34 g of Rongalite® are added and the mixture is stirred for 48 h. The insoluble matter is removed by filtration. The filtrate is washed with sodium bicarbonate solution and then with water. The organic phase is dried over sodium sulphate and concentrated. The residue is purified by silica gel column chromatography, eluting with a chloroform/acetone 95/5 mixture. 7.25 g of compound are obtained, of which a sample of 1.5 g is removed in order to be recrystallized from an N,N-dimethylformamide/water 60/40 mixture. After drying, 1.36 g of product are obtained. Melting point: 192.5°–195° C.

EXAMPLE 11 (COMPOUND NO.19).

7-Chloro-N,9-dimethyl-2-phenyl-9H-imidazo[1,2-a]benzimidazole-3-acetamide.

11.1. 7-Chloro-9-methyl-2-phenyl-9H-imidazo[1,2-a]benzimidazole-3-acetic acid.

5.61 g (0.0145 mol) of 7-chloro-N,N,9-trimethyl-2-phenyl-9H-imidazo[1,2-a]benzimidazole-3-acetamide are dissolved in 130 ml of 2-methoxyethanol, 4.7 g of sodium hydroxide and 30 ml of water are added thereto, and the mixture is then stirred and refluxed for 4 h. The solvent is evaporated under reduced pressure, and the residue is taken up in water and in acetic acid to pH=5. The precipitate formed is suspended in 100 ml of 2-methoxyethanol with 4 g of potassium hydroxide and 30 ml of water. The mixture is again refluxed for 8 h. The solvent is then evaporated under reduced pressure, and the residue is taken up in water and the solution is acidified to pH =5 with acetic acid. A precipitate is isolated and dried under vacuum; 4.52 g of product are obtained. Melting point: 230°–232° C.

11.2. 7-Chloro-N,9-dimethyl-2-phenyl-9H-imidazo[1,2-a]benzimidazole-3-acetamide.

A suspension of 1.7 g (0.005 mol) of 7-chloro-9-methyl-2-phenyl-9H-imidazo[1,2-a]benzimidazole-3-acetic acid is prepared in 50 ml of dry tetrahydrofuran, 1.3 g (0.008 mol) of N,N'-carbonyldiimidazole are added thereto and the mixture is stirred at 40° C. for 2 h. The solution obtained is treated with an excess of dry gaseous methylamine and stirred for 72 h. The solvent is evaporated under reduced pressure. The residue is treated with 50 ml of water. The insoluble matter is separated by filtration, washed with water and then dried. 1.66 g of solid are obtained which are purified by silica gel chromatography, eluting with a dichloromethane/methanol 95/5 mixture. The product is recrystallized from an N,N-dimethylformamide/water 75/25 mixture and then dried. 1.27 g of solid are obtained. Melting point: 274°–275° C.

EXAMPLE 12 (COMPOUND NO.28)

N,N,6,7,9-Pentamethyl-2-phenyl-9H-imidazo[1,2-a]benzimidazole-3-acetamide.

12.1 α-Hydroxy-N,N,6,7,9-pentamethyl-2-phenyl-9H-imidazo[1,2-a]benzimidazole-3-acetamide.

22.6 g (0.128 mol) of 2,2-diethoxy-N,N-dimethylacetamide and 3.4 ml (0.041 mol) of concentrated hydrochloric acid are dissolved in 120 ml of acetic acid, and the mixture is stirred for 1 h at 40° C. 10.7 g of sodium acetate are then added and the mixture is again stirred for 15 min at 40°–45° C. 11.86 g (0.043 mol) of N,6,7-trimethyl-2-phenyl-9H-imidazo[1,2-a]benzimidazole dissolved in 60 ml of acetic acid are then added and the mixture is stirred for 2 h at 40°–45° C. The solvent is evaporated under reduced pressure at a temperature of less than 45° C. The residue is taken up in ice-cold water and dichloromethane. The mixture is stirred for 5 min and then basified with ammonium hydroxide. A precipitate is removed by filtration. The filtrate is washed with water, and the organic phase is dried over sodium sulphate and then evaporated under reduced pressure. 7.09 g of product are isolated. The abovementioned precipitate is taken up in methanol. The suspension is filtered and the filtrate is concentrated under reduced pressure. A second batch of 5.72 g of product is obtained. The two are combined and they are used as they are in the next stage.

12.2. N,N,6,7,9-Pentamethyl-2-phenyl-9H-imidazo[1,2-a]benzimidazole-3-acetamide.

13.7 g (0.0363 mol) of α-hydroxy-N,N,6,7,9-pentamethyl- 2-phenyl-9H-imidazo[1,2-a]benzimidazole-3-acetamide are dissolved in 500 ml of dichloromethane. A slight insoluble matter is removed by filtration. 75 ml of thionyl chloride are added to the filtrate and the mixture is stirred for 3 h, allowed to stand overnight, and again stirred for 6 h. The solvent is evaporated under reduced pressure, as well as the excess thionyl chloride by means of toluene. The residue is dissolved in 500 ml of dichloromethane and 23.5 g of Rongalite® are added to this solution. The mixture is stirred for 48 h. The insoluble matter is removed by filtration, and the organic phase is washed with water, with sodium bicarbonate solution and then with water. It is dried over sodium sulphate and concentrated under reduced pressure. 12.23 g of product are obtained which are washed with ether and then purified by silica gel column chromatography, eluting with a chloroform/acetone 95/5 mixture. 6.16 g of product are obtained, of which 1.32 g are removed for two successive treatments with carbon black in methanol. 1.04 g of product are finally isolated. Melting point: 202°–206° C.

EXAMPLE 13 (COMPOUND NO.83).

2-(4-Chlorophenyl)-N,6,9-trimethyl-9H-imidazo[1,2-a]benzimidazole-3-acetamide.

13.1. 2-(4-Chlorophenyl)-α-hydroxy-N,N,6,9-tetramethyl-9H-imidazo[1,2-a]benzimidazole-3-acetamide.

25.6 g (0.146 mol) of 2,2-diethoxy-N,N-dimethylacetamide and 4 ml (0.048 mol) of concentrated hydrochloric acid are dissolved in 100 ml of acetic acid and the mixture is heated at 40° C. for 1 h. 12 g (0.146 mol) of sodium acetate are added. The mixture is stirred for 15 min, a solution of 14.4 g (0.049 mol) of 2-(4-chlorophenyl)-6,9-dimethyl-9H-imidazo[1,2-a]benzimidazole in 100 ml of acetic acid is then added and the mixture is stirred at 40° C. for 5 h. The solvent is evaporated under reduced pressure at a temperature of less than 45° C. The residue is taken up in 300 ml of ice-cold water and 300 ml of chloroform, sodium hydroxide is added, and the mixture is stirred for 5 min. Insoluble matter is removed by filtration, and the organic phase is separated and dried over sodium sulphate. The solvent is evaporated under reduced pressure. The residue is taken up in pentane, and the insoluble matter is separated by filtration, drained, washed and dried. 10.4 g of compound are obtained. Melting point: 150° C.

13.2. 2-(4-Chlorophenyl)-N,N,6,9-tetramethyl-9H-imidazo[1,2-a]benzimidazole-3-acetamide.

10.2 g (0.026 mol) of 2-(4-chlorophenyl)-α-hydroxy-N,N, 6,9-tetramethyl-9H-imidazo[1,2-a]benzimidazole-3-acetamide are treated with 50 ml of thionyl chloride in 200 ml of dichloromethane. The mixture is stirred for 3 h and allowed to stand overnight. The solvent and the excess thionyl chloride are evaporated under reduced pressure. The residue is taken up in petroleum ether, filtered off, washed and dried. It is then treated with 16 g (0.103 mol) of Rongalite® in 450 ml of dichloromethane, while stirring the mixture for 24 h. The insoluble matter is separated by filtration. The organic phase is washed with a saturated sodium hydrogen carbonate solution and then with water, dried over sodium sulphate, and filtered. The solvent is evaporated under reduced pressure. The residue is taken up in pentane, and the solid obtained is purified by silica gel column chromatography, eluting with a chloroform/acetone 93/7 mixture. 3.3 g of solid are isolated, of which 0.7 g is removed and treated with aqueous hydrochloric acid. The mixture is stirred. The solid is drained, washed with water, and taken up in an aqueous solution of sodium carbonate and chloroform. The organic phase is separated, washed with water, and dried, and the solvent is evaporated under reduced pressure. The residue is taken up in diethyl ether, drained and dried under vacuum. 0.46 g of compound is obtained. Melting point 239.5°–241.5° C.

13.3. 2-(4-chlorophenyl)-6,9-dimethyl-9H-imidazo[1,2-a]benzimidazole-3-acetic acid.

2.63 g (0.069 mol) of 2-(4-chlorophenyl)-N,N,6,9-tetramethyl- 9H-imidazo[1,2-a]benzimidazole-3-acetamide are dissolved in 80 ml of 2-methoxyethanol, 4.8 g (0.087 mol) of potassium hydroxide in solution in 15 ml of water are added and the mixture is refluxed for 9 h. The solvent is evaporated under reduced pressure. The residue is taken up in water, and the pH is adjusted to 5 with acetic acid. The insoluble matter is separated by filtration and dried. 2.7 g of solid are obtained. Melting point: 265°–270° C. (decomposition).

13.4. 2-(4-Chlorophenyl)-N,6,9-trimethyl-9H-imidazo[1,2-a]benzimidazole-3-acetamide.

Under a nitrogen stream, a suspension of 1.0 g (0.0028 mol) of 2-(4-chlorophenyl)-6,9-dimethyl-9H-imidazo[1,2-a]benzimidazole-3-acetic acid is prepared in 50 ml of dry tetrahydrofuran. 1.0 g (0.0063 mol) of N,N'-carbonyldiimidazole in solution in 50 ml of dry tetrahydrofuran is added and the mixture is stirred for 6 h. The solution is then treated with an excess of dry gaseous methylamine and again stirred for 4 h. The solvent is evaporated under reduced pressure. The residue is taken up in water, drained, washed with water and dried. 0.65 g of product is obtained which is purified by silica gel column chromatography, eluting with a chloroform/acetone 93/7 mixture. 0.26 g of compound is finally isolated. Melting point: 258°–260° C.

EXAMPLE 14 (COMPOUND NO.30)

N-Methyl-2-(4-methylphenyl)-9H-imidazo[1,2-a]benzimidazole-3-acetamide.

14.1. Ethyl α-hydroxy-2-(4-methylphenyl)-9H-imidazo[1,2-a]benzimidazole-3-acetate.

9.55 ml (0.053 mol) of ethyl 2,2-diethoxyacetate and 1.2 ml (0.013 mol) of concentrated hydrochloric acid are dissolved in 130 ml of acetic acid and the mixture is heated at 60° C. for 30 min. 4.4 g (0.053 mol) of sodium acetate are added, and the mixture is stirred for 15 min. Then 6.6 g (0.027 mol) of 2-(4-methylphenyl)-9H-imidazo[1,2-a]benzimidazole are added in small portions, and the stirring is continued at 60° C. for 5 h. The solvent is evaporated under reduced pressure. The residue is taken up in dichloromethane and dilute ammonium hydroxide. Insoluble matter is separated by filtration. The organic phase is separated, washed with water to neutral pH, and dried over sodium sulphate. The solvent is evaporated under reduced pressure, and the residue is purified by silica gel column chromatography, eluting with a dichloromethane/methanol 97/3 mixture. After recrystallization from pentane, 6.5 g of red product are obtained, which is used as it is in the next stage.

14.2. Ethyl 2-(4-methylphenyl)-9H-imidazo[1,2-a]benzimidazole-3-acetate.

6.3 g (0.018 mol) of ethyl α-hydroxy-2-(4-methylphenyl)-9H-imidazo[1,2-a]benzimidazole-3-acetate are treated with 18 ml of thionyl chloride in 180 ml of dichloromethane while stirring the mixture for 16 h. The solvent and the excess thionyl chloride are evaporated under reduced pressure. The residue is taken up in diethyl ether, washed, drained and dried. It is then treated with 7.8 g (0.051 mol) of Rongalite® in 170 ml of dichloromethane, while stirring the mixture at room temperature for 16 h. The solid is separated by filtration. The organic phase is washed with a saturated sodium hydrogen carbonate solution and then with water to neutral pH, and dried over sodium sulphate. The solvent is evaporated under reduced pressure and the residue is purified by crystallization from diethyl ether. 4.9 g of compound are obtained. Melting point: 234°–237° C. (decomposition).

14.3. N-Methyl-2-(4-methylphenyl)-9H-imidazo[1,2-a]benzimidazole-3-acetamide.

2 g of ethyl 2-(4-methylphenyl)-9H-imidazo[1,2-a]benzimidazole-3-acetate in 60 ml of methanol are treated with 60 ml of liquid methylamine, while stirring the mixture at room temperature for 16 h. The solvent is evaporated under reduced pressure. The residue is washed with water and recrystallized twice from N,N-dimethylformamide. 0.8 g of compound is finally isolated. Melting point: 303°–308° C. (decomposition).

EXAMPLE 15 (COMPOUND NO.42).

N-(2-methoxyethyl)-2-(4-methylphenyl)-9H-imidazo[1,2-a]benzimidazole-3-acetamide.

A suspension of 3.5 g (0.11 mol) of 9-methyl-2-(4-methylphenyl)-9H-imidazo[1,2-a]benzimidazole-3-acetic acid is prepared in 70 ml of dry tetrahydrofuran, 2.67 g (0.165 mol) of N,N'-carbonyldiimidazole are added in small portions, over 10 min, and the mixture is stirred at room temperature for 1 h. It is cooled in an ice-cold water bath, and 1.65 g (0.165 mol) of 2-methoxyethylamine in solution in 4 ml of dry tetrahydrofuran are added. Stirring is continued for 1 h at cold temperature, and then at room temperature for 4 h. The solvent is evaporated under reduced pressure. The residue is crystallized from water. The solid is collected by filtration, washed, dried and recrystallized from ethanol. 2.9 g of compound are finally obtained. Melting point: 189°–190° C.

Table 1 below illustrates the chemical structures and the physical properties of some compounds of formula (I).

In the "Salt" column, "-" designates a compound in base form, and "HCl" designates a compound in hydrochloride form. In the "m.p. (° C.)" column, "(d)" designates a melting temperature with decomposition.

TABLE I

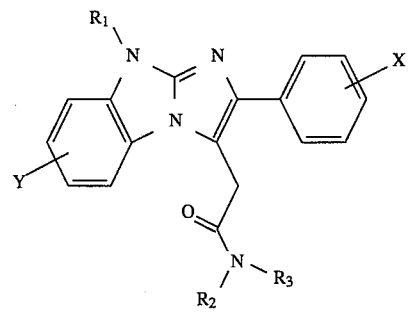
(I)

| No. | X | Y | $R_1$ | $R_2$ | $R_3$ | Salt | m.p. (°C.) |
|---|---|---|---|---|---|---|---|
| 1 | H | H | H | H | $CH_3$ | — | 316–321 (d) |
| 2 | H | H | H | $CH_3$ | $CH_3$ | — | 268–271 (d) |

TABLE I-continued

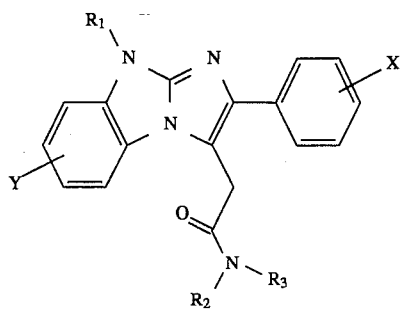
(I)

| No. | X | Y | $R_1$ | $R_2$ | $R_3$ | Salt | m.p. (°C.) | |
|---|---|---|---|---|---|---|---|---|
| 3 | H | H | $CH_3$ | H | H | — | 238–239 | |
| 4 | H | H | $CH_3$ | H | $CH_3$ | — | 253–254 | (d) |
| 5 | H | H | $CH_3$ | $CH_3$ | $CH_3$ | — | 173–175 | |
| 6 | H | H | $CO_2CH_2CH_3$ | $CH_3$ | $CH_3$ | — | 218–220 | |
| 7 | H | 6-F | H | H | $CH_3$ | — | amorphous | |
| 8 | H | 6-F | H | $CH_3$ | $CH_3$ | — | amorphous | |
| 9 | H | 6-$CH_3$ | $CH_3$ | H | H | — | 247–249 | (d) |
| 10 | H | 6-$CH_3$ | $CH_3$ | H | $CH_3$ | — | 251–253 | |
| 11 | H | 6-$CH_3$ | $CH_3$ | $CH_3$ | $CH_3$ | — | 222–223 | |
| 12 | H | 6-Br | $CH_3$ | H | H | — | 268.5–270 | |
| 13 | H | 6-Br | $CH_3$ | H | $CH_3$ | — | 272–280 | (d) |
| 14 | H | 6-Br | $CH_3$ | $CH_3$ | $CH_3$ | — | 246.5–248 | |
| 15 | H | 6-Cl | $CH_3$ | H | H | — | 253–254 | (d) |
| 16 | H | 6-Cl | $CH_3$ | H | $CH_3$ | — | 272–273.5 | (d) |
| 17 | H | 6-Cl | $CH_3$ | $CH_3$ | $CH_3$ | — | 233–236 | |
| 18 | H | 7-Cl | $CH_3$ | H | H | — | 254.5–356.5 | (d) |
| 19 | H | 7-Cl | $CH_3$ | H | $CH_3$ | — | 274–275 | |
| 20 | H | 7-Cl | $CH_3$ | $CH_3$ | $CH_3$ | — | 192.5–195 | |
| 21 | H | 6-F | $CH_3$ | H | H | — | 244–245 | (d) |
| 22 | H | 6-F | $CH_3$ | H | $CH_3$ | — | 256.6–258 | |
| 23 | H | 6-F | $CH_3$ | $CH_3$ | $CH_3$ | — | 201.5–202.5 | |
| 24 | H | 6-$OCF_3$ | $CH_3$ | $CH_3$ | $CH_3$ | — | 139.5–141 | |
| 25 | H | 6-$C(CH_3)_3$ | $CH_3$ | $CH_3$ | $CH_3$ | — | amorphous | |
| 26 | H | 6,7-$(CH_3)_2$ | $CH_3$ | H | H | — | 238.5–239 | (d) |
| 27 | H | 6,7-$(CH_3)_2$ | $CH_3$ | H | $CH_3$ | — | 275–276 | (d) |
| 28 | H | 6,7-$(CH_3)_2$ | $CH_3$ | $CH_3$ | $CH_3$ | — | 202–206 | |
| 29 | H | 6,7-$Cl_2$ | $CH_3$ | $CH_3$ | $CH_3$ | — | 209–217 | (d) |
| 30 | 4-$CH_3$ | H | H | H | $CH_3$ | — | 303–308 | (d) |
| 31 | 4-$CH_3$ | H | H | $CH_3$ | $CH_3$ | — | 280–288 | (d) |
| 32 | 2-$CH_3$ | H | $CH_3$ | H | H | — | 213–214.5 | |
| 33 | 2-$CH_3$ | H | $CH_3$ | H | $CH_3$ | — | 213–215 | |
| 34 | 2-$CH_3$ | H | $CH_3$ | $CH_3$ | $CH_3$ | — | 135–137 | |
| 35 | 3-$CH_3$ | H | $CH_3$ | H | H | — | 235–238 | |
| 36 | 3-$CH_3$ | H | $CH_3$ | H | $CH_3$ | — | 234–236 | |
| 37 | 3-$CH_3$ | H | $CH_3$ | $CH_3$ | $CH_3$ | — | 178–179 | |
| 38 | 4-$CH_3$ | H | $CH_3$ | H | H | — | 258–260 | |
| 39 | 4-$CH_3$ | H | $CH_3$ | H | $CH_3$ | — | 251–252 | |
| 40 | 4-$CH_3$ | H | $CH_3$ | H | $CH_2CH_3$ | — | 238–240 | |
| 41 | 4-$CH_3$ | H | $CH_3$ | H | $CH_2CH_2CH_3$ | — | 237–239 | |
| 42 | 4-$CH_3$ | H | $CH_3$ | H | $CH_2CH_2OCH_3$ | — | 189–190 | |
| 43 | 4-$CH_3$ | H | $CH_3$ | H | $CH_2CH_2OC_6H_5$ | — | 220–221 | |
| 44 | 4-$CH_3$ | H | $CH_3$ | H | [imidazolylethyl group] | — | 170–172 | |
| 45 | 4-$CH_3$ | H | $CH_3$ | H | [4-methylpiperidinyl-methyl-cyclohexenyl group] | — | 214–257 | |
| 46 | 4-$CH_3$ | H | $CH_3$ | H | [4-methylpiperidinyl-benzyl group] | — | 226–228 | |
| 47 | 4-$CH_3$ | H | $CH_3$ | $CH_3$ | $CH_3$ | — | 195–196 | |

TABLE I-continued
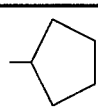
(I)
| No. | X | Y | R₁ | R₂ | R₃ | Salt | m.p. (°C.) |
|---|---|---|---|---|---|---|---|
| 48 | 4-CH₃ | H | CH₃ | H |  | — | 257–258.5 |
| 49 | 4-CH₃ | H | CH₃ | 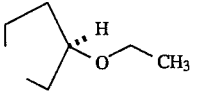 |  | — | 190–192 |
| 50 | 4-CH₃ | H | CH₃ |  |  | — | 164–166 |
| 51 | 4-CH₃ | H | CH₃ | 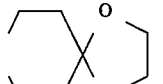 |  | — | 230–231.5 |
| 52 | 4-CH₃ | H | CH₃ | 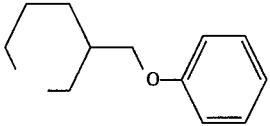 |  | — | 195–196 |
| 53 | 4-CH₃ | H | CH₃ | 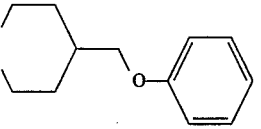 |  | HCl | 234–236 |
| 54 | 4-CH₃ | H | CH₃ | 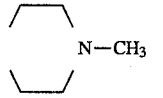 |  | — | 199–201 |
| 55 | 4-CH₃ | H | CH₃ | 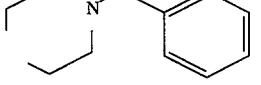 |  | — | 222–224 |
| 56 | 4-CH₃ | H | CH₃ |  |  | — | 162.5–163 |
| 57 | 4-CH₃ | H | CH₂CH₃ | H | H | — | 251–254 (d) |
| 58 | 4-CH₃ | H | CH₂CH₃ | H | CH₃ | HCl | 235–238 (d) |
| 59 | 4-CH₃ | H | CH₂CH₃ | CH₃ | CH₃ | HCl | 247–251 (d) |
| 60 | 4-CH₃ | H | CH₂C₆H₅ | H | H | — | 279–284 (d) |
| 61 | 4-CH₃ | H | CH₂C₆H₅ | H | CH₃ | — | 222–225 |
| 62 | 4-CH₃ | H | CH₂C₆H₅ | CH₃ | CH₃ | — | 189–190 |
| 63 | 4-CH₃ | H | COCH₃ | CH₃ | CH₃ | — | 235–237 |
| 64 | 4-CH₃ | 6-Cl | CH₃ | H | H | — | amorphous |
| 65 | 4-CH₃ | 6-Cl | CH₃ | H | CH₃ | — | amorphous |
| 66 | 4-CH₃ | 6-Cl | CH₃ | CH₃ | CH₃ | — | 224–225 |
| 67 | 4-CF₃ | H | CH₃ | H | H | — | 295–303 (d) |

TABLE I-continued

| No. | X | Y | $R_1$ | $R_2$ | $R_3$ | Salt | m.p. (°C.) | |
|---|---|---|---|---|---|---|---|---|
| 68 | 4-$CF_3$ | H | $CH_3$ | H | $CH_3$ | — | 272–276 | (d) |
| 69 | 4-CFhd 3 | H | $CH_3$ | $CH_3$ | $CH_3$ | — | 220–221 | |
| 70 | 4-$CH_2CH_3$ | H | $CH_3$ | H | H | — | 263–265 | (d) |
| 71 | 4-$CH_2CH_3$ | H | $CH_3$ | H | $CH_3$ | — | 214–215 | |
| 72 | 4-$CH_2CH_3$ | H | $CH_3$ | $CH_3$ | $CH_3$ | — | 133–135 | |
| 73 | 4-Cl | H | H | H | $CH_3$ | HCl | 298–303 | (d) |
| 74 | 4-Cl | H | H | $CH_3$ | $CH_3$ | — | 287–289 | |
| 75 | 3-Cl | H | $CH_3$ | H | H | — | 266–268 | (d) |
| 76 | 3-Cl | H | $CH_3$ | H | $CH_3$ | — | 268.5–271 | (d) |
| 77 | 3-Cl | H | $CH_3$ | $CH_3$ | $CH_3$ | — | 222–223 | |
| 78 | 4-Cl | H | $CH_3$ | H | H | — | 270–272 | (d) |
| 79 | 4-Cl | H | $CH_3$ | H | $CH_3$ | — | 252–253.5 | |
| 80 | 4-Cl | H | $CH_3$ | $CH_3$ | $CH_3$ | — | 229–229.5 | |
| 81 | 4-Cl | H | $CH_3$ | $CH_2CH_2CH_3$ | $CH_2CH_2CH_3$ | — | 155–157 | |
| 82 | 4-Cl | 6-$CH_3$ | $CH_3$ | H | H | — | >300 | |
| 83 | 4-Cl | 6-$CH_3$ | $CH_3$ | H | $CH_3$ | — | 258–260 | |
| 84 | 4-Cl | 6-$CH_3$ | $CH_3$ | $CH_3$ | — | 239.5–241.5 | | |
| 85 | 4-Cl | 6-Cl | $CH_3$ | H | H | — | 299–303 | |
| 86 | 4-Cl | 6-Cl | $CH_3$ | H | $CH_3$ | — | 273–275 | (d) |
| 87 | 4-Cl | 6-Cl | $CH_3$ | $CH_3$ | $CH_3$ | — | 235–235.5 | |
| 88 | 4-F | H | H | H | $CH_3$ | HCl | 279–280.5 | (d) |
| 89 | 4-F | H | H | $CH_3$ | $CH_3$ | HCl | 297.5–300 | (d) |
| 90 | 4-F | H | $CH_3$ | H | H | — | 270.5–273.5 | |
| 91 | 4-F | H | $CH_3$ | H | $CH_3$ | — | 235–236.5 | |
| 92 | 4-F | H | $CH_3$ | $CH_3$ | $CH_3$ | — | 224–225 | |
| 93 | 4-F | 6-$CH_3$ | $CH_3$ | H | H | — | 268–270 | (d) |
| 94 | 4-F | 6-$CH_3$ | $CH_3$ | H | $CH_3$ | — | 255–256 | |
| 95 | 4-F | 6-$CH_3$ | $CH_3$ | $CH_3$ | $CH_3$ | — | 249–250 | |
| 96 | 4-F | 6-Cl | $CH_3$ | H | H | — | 290–291 | |
| 97 | 4-F | 6-Cl | $CH_3$ | H | $CH_3$ | — | 269–270 | |
| 98 | 4-F | 6-Cl | $CH_3$ | $CH_3$ | $CH_3$ | — | 262–263 | |
| 99 | 4-$OCH_3$ | H | $CH_3$ | H | H | — | 242–244 | |
| 100 | 4-$OCH_3$ | H | $CH_3$ | H | $CH_3$ | — | 248–249.5 | |
| 101 | 4-$OCH_3$ | H | $CH_3$ | $CH_3$ | $CH_3$ | — | 154–155 | |
| 102 | 4-$SCH_3$ | H | $CH_3$ | H | H | — | 260–263 | (d) |
| 103 | 4-$SCH_3$ | H | $CH_3$ | H | $CH_3$ | — | 264–266 | (d) |
| 104 | 4-$SCH_3$ | H | $CH_3$ | $CH_3$ | $CH_3$ | — | 190.5–192 | |
| 105 | 4-$SO_2CH_3$ | H | $CH_3$ | $CH_3$ | $CH_3$ | — | amorphous | |
| 106 | 4-$CH_3$ | H | $CH_3$ | H | $C_6H_5$ | — | 268–270 | (d) |
| 107 | 4-$CH_3$ | H | $CH_3$ | H | $CH_2C_6H_5$ | — | 232–238 | |
| 108 | 4-$CH_3$ | H | $CH_3$ | H | $CH_2CH_2N(CH_3)_2$ | — | 196–197 | |
| 109 | 4-$CH_3$ | H | $CH_3$ | | | — | 181.5–183 | |
| 110 | 4-$CO_2C_2H_5$ | H | $CH_3$ | H | $CH_3$ | — | 238–239 | |
| 111 | 4-$CONH_2$ | H | $CH_3$ | H | $CH_3$ | — | 277–279 | (d) |
| 112 | 4-$CO_2H$ | H | $CH_3$ | H | $CH_3$ | — | 269–270 | |

Table 2 below illustrates the chemical structures and physical properties of some compounds of general formula (IV), which are intermediates in the process of Scheme 1. All the compounds are in base form. In the "m.p. (° C.)" column, "(d)" designates a melting temperature with decomposition, and "(l/d)" designates a slow melting temperature with decomposition.

TABLE 2

(IV)

| No. | X | Y | R₁ | m.p. (°C.) | |
|-----|---|---|-----|------------|---|
| 1' | H | H | CH₃ | 241–244 | (d) |
| 2' | H | 6-CH₃ | CH₃ | 210–215(*) | (1/d) |
| 3' | H | 6-Br | CH₃ | 245–250 | (1/d) |
| 4' | H | 6-Cl | CH₃ | 245–250 | (1/d) |
| 5' | H | 7-Cl | CH₃ | 230–232 | (1/d) |
| 6' | H | 6-F | CH₃ | 252–254 | (1/d) |
| 7' | H | 6-OCF₃ | CH₃ | | |
| 8' | H | 6,7-(CH₃)₂ | CH₃ | 220 | (1/d) |
| 9' | 2-CH₃ | H | CH₃ | 262–264 | (d) |
| 10' | 3-CH₃ | H | CH₃ | 212–218 | (d) |
| 11' | 4-CH₃ | H | CH₃ | 250–254 | (d) |
| 12' | 4-CH₃ | H | CH₂CH₃ | 216–218 | (d) |
| 13' | 4-CH₃ | CH₂Chd 6H₅ | CH₃ | 233–239 | (1/d) |
| 14' | 4-CH₃ | 6-Cl | CH₃ | | |
| 15' | 4-CFhd 3 | H | CH₃ | 250–253 | (d) |
| 16' | 4-CH₂CH₃ | H | CH₃ | 250–252 | (d) |
| 17' | 3-Cl | H | CH₃ | 210–215 | (d) |
| 18' | 4-Cl | H | CH₃ | 252–255 | (d) |
| 19' | 4-Cl | 6-CH₃ | CH₃ | 265–270 | (d) |
| 20' | 4-Cl | 6-Cl | CH₃ | 260–265 | (d) |
| 21' | 4-F | H | CH₃ | 261–266 | (1/d) |
| 22' | 4-F | 6-CH₃ | CH₃ | 223–225 | (d) |
| 23' | 4-F | 6-Cl | CH₃ | 258–260 | (d) |
| 24' | 4-OCH₃ | H | CH₃ | 220–222 | (d) |
| 25' | 4-SCH₃ | H | CH₃ | 249–252 | (d) |

(*)Compound number 2' has a first melting point at 150–155° C., beyond wihich it recrystallizes.

Table 3 below illustrates the chemical structures and physical properties of some compounds of formula (VI), which are intermediates in the process of Scheme 2. All the compounds are in the form of bases. In the "m.p. (° C.)" column, "(d)" designates a melting temperature with decomposition.

TABLE 3

(VI)

| No. | X | Y | R₁ | m.p. (°C.) | |
|-----|---|---|-----|------------|---|
| 1" | H | H | H | 220–222 | |
| 2" | H | 6-F | H | | |
| 3" | 4-CH₃ | H | H | 234–237 | (d) |
| 4" | 4-Cl | H | H | 260–261 | |
| 5" | 4-F | H | H | 245–247 | (d) |

The compounds of the invention have been subjected to pharmacological trials which have demonstrated their usefulness as substances with therapeutic activity.

Study of membrane bindings with respect to the $\omega_1$ (type 1 benzodiazepines) and $\omega_2$ (type 2 benzodiazepines) receptors.

The affinity of the compounds for the $\omega_1$ receptors of the cerebellum and the $\omega_2$ receptors of the spinal cord was determined according to a variant of the method described by S. Z. Langer and S. Arbilla in Fund. Clin. Pharmacol., 2, 159–170 (1988), with the use of $^3$H-flumazenil instead of $^3$H-diazepam as radioligand. The cerebellum or spinal cord tissue is homogenized for 60 s in 120 or 30 volumes, respectively, of ice cold buffer (50 mM Tris/HCl, pH 7.4, 120 mM NaCl, mM KCl) and then, after a 1/3 dilution, the suspension is incubated with $^3$H-flumazenil (specific activity 78 Ci/mmol, New England Nuclear) at a concentration of 1 nM and with the compounds of the invention at various concentrations, in a final volume of 525 μl. After incubating for 30 minutes at 0° C., the samples are filtered under vacuum on Whatman GF/B® filters and they are washed immediately with ice cold buffer. The specific binding of $^3$H-flumazenil is determined in the presence of 1 μM unlabelled diazepam. The data are analysed according to the usual methods and the IC$_{50}$ concentration, the concentration which inhibits the binding of $^3$-flumazenil by 50%, is calculated. The IC$_{50}$ values for the compounds of the invention are situated, in these trials, between 1 and 300 nM.

Study of the hypnotic activity.

The sedative or hypnotic activity of the compounds was determined by observing their action on rat electrocorticogram, according to the method described by H. Depoortere, Rev. E. E. G. Neurophysiol., 10, 3, 207–214 (1980) and by H. Depoortere and M. Decobert, J. Pharmacol. (Paris), 14, 2, 195–265 (1983). The products to be studied were administered intraperitoneally at increasing doses. They induce sleep tracings at doses ranging from 0.1 to 30 mg/kg.

Study of the anxiolytic activity

The anxiolytic activity is evaluated on rats in the test of conflict for the consumption of water, according to the method described by J. R. Vogel, B. Beer and D. E. Clody in Psychopharmacologia (Berl.), 21, 1–7 (1971). After a water diet for 48 h, the rat is placed in a chamber insulated from noise and equipped with a water pipette connected to an anxiometer delivering a slight electric shock every 20 laps of the tongue. The number of shocks received is automatically counted for 3 minutes, and makes it possible to evaluate the anxiolytic activity of the tested compounds. The results are expressed as minimal effective dose (MED), the dose which produces a significant increase in the number of shocks received, compared with the number observed in the control animals. The MED values of the compounds of the invention are situated, in this trial, between 1 and 50 mg/kg by the intraperitoneal or oral route.

Study of the anticonvulsant activity.

Activity with respect to the maximum convulsions induced in mice by electroshock or by injection of pentetrazole.

The procedure for this trial is described by E. A. Swinyard and J. H. Woodhead in Antiepileptic Drugs, Raven Press, New York, 111 –126 (1982). 30 minutes after intraperitoneal administration of the test compound, the number of mice having convulsions (extensions of the hind legs) is noted, either immediately after application of an electric current (0.4 s, 60 mA, 50 Hz) by means of transcorneal electrodes, or for the 30 minutes which follow the subcutaneous injection of pentetrazole (125 mg/kg). The results are expressed as the AD$_{50}$, the dose which protects 50% of the animals, calculated according to the method of J. T. Litchfield and F. Wilcoxon (J. Pharm. Exp. Ther., 96, 99–113 (1949)) based on 3 or 4 doses, each administered to a group of 8 to 10 mice.

The $AD_{50}$ values for the compounds of the invention are situated, in this trial, between 1 and 100 mg/kg by the intraperitoneal route.

Study of the anticonvulsant activity.

Activity with respect to the convulsions induced in mice by isoniazide.

The intrinsic activity of the compounds is determined by the latent period for the onset of convulsions induced by the subcutaneous administration of isoniazide (800 mg/kg) simultaneously with the test compound, injected intraperitoneally, according to the procedure described by G. Perrault, E. Morel, D. Sanger and B. Zivkovic in Eur. J. Pharmacol., 156, 189–196 (1988). The results are expressed as $AD_{50}$, the dose which produces 50% of the maximum effect, compared with the control animals, which is determined based on 3 or 4 doses each administered to a group of 8 to 10 mice. The $AD_{50}$ values for the compounds of the invention are situated, in this trial, between 1 and 50 mg/kg by the intraperitoneal route and, according to the compounds, the maximum effect may range up to 350%.

The results of the trials carried out on the compounds of the invention show that, in vitro, they displace $^3$H-flumazenil from its specific binding sites in the cerebellum and the spinal cord; consequently, they exhibit an affinity for the $\omega_1$ and $\omega_2$ sites (type 1 and type 2 benzodiazepines) situated within the macromelecular complex $GABA_A$-$\omega$ sites-chloride channel. In vivo they behave like total or partial agonists, or like antagonists towards these receptors. They possess hypnotic, anxiolytic and anticonvulsant properties and, consequently, they can be used for the treatment of conditions associated with GABAergic transmission disorders, such as anxiety, sleep disorders, epilepsy, spasticity, muscle contractures, cognitive disorders, alcohol withdrawal disorders, and the like. Finally, they can be used in premedication and as general anaesthetics for inducing and/or maintaining anaesthesia, or as local anaesthetics, optionally combined with other anaesthetics and/or muscle relaxants and/or analgesics.

To this effect, they can be provided in any galenical forms, combined with appropriate excipients, for enteral or parenteral adminstration, for example in the form of tablets, sugar-coated tablets, hard gelatine capsules, capsules, solutions or suspensions to be taken orally or for injection, suppositories, and the like, containing doses which permit a daily administration of 1 to 1000 mg of active substance.

We claim:

1. A Compound of the formula:

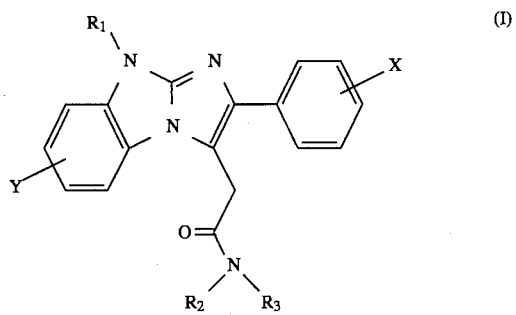

in which

X represents one or more atoms or groups chosen from hydrogen, fluorine, chlorine, bromine, $(C_1$-$C_3)$alkyl, trifluoromethyl, $(C_1$-$C_3)$alkoxy, $(C_1$-$C_3)$alkylthio, methylsulphonyl, cyano, ethoxycarbonyl, aminocarbonyl and carboxy, Y represents one or more atoms or groups chosen from hydrogen, fluorine, chlorine, bromine, $(C_1$-$C_4)$alkyl, trifluoromethyl, methoxy and trifluoromethoxy, $R_1$ represents hydrogen atom, $(C_1$-$C_3)$alkyl, phenylmethyl, 2-phenylethyl, acetyl, or $(C_1$-$C_3)$alkoxycarbonyl, $R_2$ and $R_3$ are the same or different and each represents: hydrogen; $(C_1$-$C_5)$alkyl which is linear, branched or cyclic, and optionally substituted by one or more fluorine atoms, or by methoxy, phenoxy, dimethylamino, phenyl, prop-2-enyl; prop-2-ynyl; phenyl in the form of a free base or an acid addition salt.

2. A compound according to claim 1, in which X is in position 4 and represents hydrogen, fluorine or methyl.

3. A compound according to claim 1, in which Y is in position 6 and represents hydrogen, fluorine or methyl.

4. A compound according to claim 1, in which $R_1$ is hydrogen or methyl.

5. A compound according to claim 1, in which $R_2$ and $R_3$ each represent, independently of one another, hydrogen or methyl.

6. Pharmaceutical composition comprising a compound according to claim 1 combined with an excipient.

7. Method of producing a hypnotic, anxiolytic, or anticonvulsant effect in a patient which comprises administering to said patient an effective amount of a compound as claimed in claim 1.

* * * * *